United States Patent [19]

Takano

[11] Patent Number: 4,940,722
[45] Date of Patent: * Jul. 10, 1990

[54] SEED DISINFECTANT COMPOSITION

[75] Inventor: Hirotaka Takano, Nishinomiya, Japan

[73] Assignee: Sumitomo Chemical Companmy, Limited, Osaka, Japan

[*] Notice: The portion of the term of this patent subsequent to Oct. 21, 2003 has been disclaimed.

[21] Appl. No.: 122,858

[22] Filed: Nov. 17, 1987

[30] Foreign Application Priority Data

Dec. 10, 1986 [JP] Japan ................................ 61-293771

[51] Int. Cl.$^5$ ...................... A01N 43/52; A01N 43/64
[52] U.S. Cl. ..................................... 514/383; 514/388
[58] Field of Search ................................ 514/383, 388

[56] References Cited

U.S. PATENT DOCUMENTS

| | | |
|---|---|---|
| 4,251,512 | 2/1981 | Brandes et al. |
| 4,285,722 | 8/1981 | Worthington et al. ............. 424/269 |
| 4,331,675 | 5/1982 | Regel et al. .......................... 424/269 |
| 4,435,203 | 3/1984 | Funaki et al. ........................ 424/269 |
| 4,618,620 | 10/1986 | Ishiguri ................................ 514/383 |

FOREIGN PATENT DOCUMENTS

| | | |
|---|---|---|
| 0054431 | 6/1982 | European Pat. Off. |
| 0095242 | 11/1983 | European Pat. Off. |
| 2332707 | 6/1977 | France . |
| 2046260 | 11/1980 | United Kingdom . |

OTHER PUBLICATIONS

Chemical Abstracts, vol. 100, No. 25, 18 Jun. 1984, p. 193, Abstract No. 204987v.
The Pesticide Manual, 6th Edition, pp. 32, 80, 288, 509, 517 and 518 (1979).
Systemic Fungicides, pp. 64–67, 78–81 (1972).

*Primary Examiner*—Paul Lieberman
*Assistant Examiner*—John F. McNally
*Attorney, Agent, or Firm*—Stevens, Davis, Miller & Mosher

[57] ABSTRACT

A seed disinfectant composition comprising
  (A) (E)-1-(2,4-dichlorophenyl)-4,4-dimethyl-2-(1,2,4-triazol-1-yl)-1-penten-3-ol containing not less than 50% by weight of (−)-(E)-1-(2,4-dichlorophenyl)-4,4-dimethyl-2-(1,2,4-triazol-1-yl)-1-penten-3-ol and
  (B) At least one benzimidazole thiophanate fungicide and optionally comprising
  (C) O,O-dimethyl-O-(2,6-dichloro-4-methylphenyl)-phosphorothioate and/or
  (D) 1-Ethyl-1,4-dihydro-6,7-methylenedioxy-4-oxo-3-quinoline carboxylic acid or a salt thereof are disclosed. The seed disinfectant composition of the present invention exhibits a synergistically high preventing effect on various seed born diseases and simultaneously has a wide antifungal spectrum and shows a stable preventing effect on the fungi having resistance to conventional disinfectants.

19 Claims, No Drawings

SEED DISINFECTANT COMPOSITION

The present invention relates to a seed disinfectant composition comprising (E)-1-(2,4-dichlorophenyl)-4,4-dimethyl-2-(1,2,4-triazol-1-yl)-1-penten-3-ol containing not less than 50% by weight of (-)-(E)-1-(2,4-dichlorophenyl)-4,4-dimethyl-2-(1,2,4-triazol-1-yl)-1-penten-3-ol (hereinafter referred to as Compound A) and at least one benzimidazole thiophanate fungicide (hereinafter referred to as Compound B) and optionally comprising O,O-dimethyl-O-(2,6-dichloro-4-methylphenyl)phosphorothioate (hereinafter referred to as Compound C) and/or 1-ethyl-1,4-dihydro-6,7-methylenedioxy-4-oxo-3-quinoline carboxylic acid (hereinafter referred to as Compound D) or a salt thereof.

Heretofore, benomyl thiophanate-methyl, thiram, carboxin, PCNB, organic mercury and admixtures thereof have been used to prevent seed born diseases.

However, the commercially available disinfectants mentioned above have effects only on limited diseases, and such a problem arises that these disinfectants lose their effects of preventing seed born diseases on resistant fungi which have appeared among the disease on which these disinfectants had antifungal effects before.

In view of this situation, the present inventor have made extensive research to develop a seed disinfectant having a wide antifungal spectrum and showing a stable effect of preventing diseases on the above-mentioned resistant fungi.

As a result, it has been found that a seed disinfectant composition comprising Compound A and Compound B in a specific weight ratio and optionally comprising Compound C and/or Compound D or a salt thereof in a specific weight ratio have not only all the properties mentioned above but also an excellent synergistic effect.

Thus, according to the present invention, there is provided a seed disinfectant composition comprising effective amount of (A) (E)-1-(2,4-dichlorophenyl)-4,4-dimethyl-2-(1,2,4-triazol-1-yl)-1-penten-3-ol containing not less than 50% by weight of (-)-(E)-1-(2,4-dichlorophenyl)-4,4-dimethyl-2-(1,2,4-triazol-1-yl)-1-penten-3-ol and (B) at least one benzimidazole thiophanate fungicide, wherein the weight ratio of (A):(B) is 1-50:1-50.

Compound A, one of the active ingredients of the seed disinfectant composition of the present invention, is a compound selected from the group consisting of the compounds disclosed in Japanese Patent Application Kokai (Laid-Open) Nos. 124,771/80 and 99,575/82. In other words, Compound A may be a racemic compound, a racemic mixture containing more than 50% by weight of (-)-(E)-1-(2,4-dichlorophenyl)-4,4-dimethyl-2-(1,2,4-triazol-1-yl)-1-penten-3-ol and a pure (-)-(E)-1-(2,4-dichlorophenyl)-4,4-dimethyl-2-(1,2,4-triazol-1-yl)-1-penten-3-ol.

From the viewpoint of exertion of disinfectant properties, it is preferable that Compound A contains not less than 50% by weight of (-)-(E)-1-(2,4-dichlorophenyl)-4,4-dimethyl-2-(1,2,4-triazol-1-yl)-1-penten-3-ol (hereinafter referred to as (-)-enantiomer), and since the more Compound A contains (-)-enantiomer, the greater the disinfectant effect becomes, it is more preferable that Compound A contains not less than 80% by weight of (-)-enantiomer, most preferably, it is substantially pure (-)-enantiomer (purity: 90% by weight or more).

Known benzimidazole thiophanate fungicides can be used in the present invention. However, preferable members are methyl 1-(butylcarbamoyl)benzimidazole-2-ylcarbamate (common name: benomyl, hereinafter referred to as Compound I), 2-(4-thiazolyl)benzimidazole (common name: thiabendazole, hereinafter referred to as Compound II), methyl benzimidazol-2-ylcarbamate (common name: carbendazim, hereinafter referred to as Compound III), 2-(2-furyl)benzimidazole (common name: fubelidazol, hereinafter referred to as Compound IV), 1,2-bis(3-methoxycarbonyl-2-thioureido)benzene (common name: thiophanate-methyl, hereinafter referred to as Compound V), 1,2-bis(3-ethoxycarbonyl-2-thioureido)benzene (common name: thiophanate, hereinafter referred to as Compound VI), methyl 1-(2-cyclohexenylcarbamoyl)-2-benzimidazolecarbamate (hereinafter referred to as Compound VII) and the like. Compounds I to VI are known as fungicides for various diseases of fruit trees, vegetables, barley, wheat, oats, rye and the like. Compound VII is disclosed in Japanese Patent Application Kokai (Laid-Open) No. 10,004/87.

The weight ratio of Compound A to Compound B is usually 1-50:1-50, preferably 1-20:1-20.

Compound C used in the present invention is O,O-dimethyl-O-(2,6-dichloro-4-methylphenyl)phosphorothioate disclosed in Japanese Patent Publication Kokoku (Post-Exam) No. 20,571/76.

Compound D is 1-ethyl-1,4-dihydro-6,7-methylenedioxy-4-oxo-3-quinoline carboxylic acid disclosed in Japanese Patent Application Kokai (Laid-Open) No. 48,042/82.

In the present invention, Compound A, Compound B, Compound C and Compound D are referred to as active ingredients.

The weight ratio of Compound A:Compound B:Compound C:Compound D is usually 1-50:1-50:0-50:0-50, preferably 1-20:1-20:1-20:1-20. In the present invention, they are mixed together and used.

The mixture of the active ingredients in the present invention can be used as it is, though it is usually used in admixture with an inert carrier. If necessary, various adjuvants for formulation are added such as surface active agents, wetting agents, dispersing agents, sticking agents, thickeners, stabilizers and the like depending upon the use, to formulate the seed disinfectant to a preparation such as a wettable powder, a dust, a flowable concentrate, an emulsifiable concentrate or the like.

The carriers in the above preparation include solid carriers such as a fine powder, a granule and the like of kaoline clay, attapulgite clay, bentonite, acid clay, pyrophylite, talc, diatomaceous earth, calcite, walnut shell powder, urea, ammonium sulfate, synthetic hydrous silica, white carbon and the like and liquid carriers such as, for example, xylene, methylnaphthalene and the like; alcohols, for example, isopropanol, ethylene glycol, cellosolve and the like; ketones, for example, acetone, cyclohexanone, isophorone and the like; vegetable oils such as soy oil, cottonseed oil and the like; dimethyl sulfoxide; acetonitrile; water; etc.

Surface active agents used for emulsifying, dispersing, wetting-spreading and the like include anionic surface active agents such as alkylsulfuric esters, alkyl sulfonates, aryl sulfonates, dialkyl sulfosuccinates, polyoxyethylene alkyl aryl ether phosphoric esters, naphthalene sulfonic acid-formaldehyde condensates and the like and nonionic surface active agents such as polyoxyethylene alkyl ethers, polyoxyethylene alkylaryl ethers, polyoxyethylene-polyoxypropylene block copolymers, sorbitan fatty acid esters, polyoxyethylene sorbitan fatty acid esters and the like.

Adjuvants other than the above surface active agents for formulation are lignin sulfate, lignin sulfonates alginate, poly(vinyl alcohol), gum arabic, CMC (carboxymethyl cellulose), PAP (acid isopropyl phosphate) and the like.

Other disinfectant, if necessary, such as nuarimol, hydroxyisoxazole basic copper chloride, imazalil and the like can be added thereto. Also, when anthraquinone is added thereto, the resulting disinfectant composition has a bird repellent effect, and the seed disinfectant composition of the present invention can be used in admixture with other seed-treating agents.

The content of the active ingredients in these formulations is preferably 0.1–99.9% by weight, more preferably 0.1–80% by weight.

The seed disinfectant composition of the present invention can be used for dust-coating, dipping or spraying.

In the case of dust-coating or spraying seeds with the seed disinfectant composition of the present invention, the amount of the composition used is preferably from 0.00005 to 1% as the active ingredients based on the dry weight of seeds, while in the case of dipping or spraying seeds in or with the seed disinfectant composition of the present invention, the concentration of the active ingredients in the composition is preferably from 0.01 ppm to 10%. However, the amount of the composition used is variable depending on the type of preparation or the kind of seed of crop to be treated.

The seed disinfectant composition of the present invention exhibits a synergistically high preventing effect on various seed born diseases and simultaneously has a wide antifungal spectrum and shows a stable preventing effect on the fungi having resistance to conventional disinfectants.

The seed disinfectant composition of the present invention is effective on the seed born diseases such as Erysiphe sp., Puccinia sp., *Septoria tritici, Leptosphaeria nodorum, Tilletia caries, Ustilago tritici,* Fusarium sp., *Cochliobolus sativus, Helminthosporium gramineum, Ustilago nuda, Pyrenophora teres, Rhynchosporium secalis,* Septoria sp., *Ustilago hordei, Ustilago avenae, Pyrenophora avenae, Fusarium nivale, Pyricularia oryzae, Cochliobolus miyabeanus, Gibberella fujikuroi, Pseudomonas glumae* and the like.

The present invention is explained in more detail in the following examples which are by way of illustration and not by way of limitation. In the following examples, "parts" or "%" is by weight.

Formulation Example 1 (A Dust)

0.05 part of Compound A, 0.05 part of Compound I, 20 parts of hydroxyisoxazole, 66.5 parts of kaoline clay and 13.4 parts of talc were thoroughly ground and mixed together to obtain a dust of the present invention having an active ingredient concentration of 0.1%.

Formulation Example 2 (A Dust)

2 parts of Compound A, 10 parts of Compound VII, 10 parts of Compound C, 68 parts of kaoline clay and 10 parts of talc were thoroughly ground and mixed together to obtain a dust of the present invention having an active ingredient concentration of 22%.

Formulation Example 3 (A Dust)

20 parts of Compound A, 20 parts of Compound II, 20 parts of Compound C, 20 parts of Compound D, 20 parts of kaoline clay and 10 parts of talc were thoroughly ground and mixed together to obtain a dust of the present invention having an active ingredient concentration of 80%.

Formulation Example 4 (A Wettable Powder)

0.2 part of Compound A, 2 parts of Compound III, 0.3 part of imazalil, 42.5 parts of diatomaceous earth, 50 parts of white carbon, 3 parts of sodium lauryl sulfate (a wetting agent) and 2 parts of calcium lignin sulfonate (a dispersant) were thoroughly ground and mixed together to obtain a wettable powder of the present invention having an active ingredient concentration of 2.2%.

Formulation Example 5 (A Wettable Powder)

2 parts of Compound A, 0.1 part of Compound IV, 5 parts of Compound C, 42.9 parts of diatomaceous earth, 45 parts of white carbon, 3 parts of sodium lauryl sulfate (a wetting agent) and 2 parts of calcium lignin sulfonate (a dispersant) were thoroughly ground and mixed together to obtain a wettable powder of the present invention having an active ingredient concentration of 7.1%.

Formulation Example 6 (A Wettable Powder)

0.5 part of Compound A, 5 parts of Compound V, 10 parts of Compound C, 10 parts of Compound D, 35 parts of diatomaceous earth, 34.5 parts of white carbon, 3 parts of sodium lauryl sulfate (a wetting agent) and 2 parts of calcium lignin sulfonate (a dispersant) were thoroughly ground and mixed together to obtain a wettable powder of the present invention having an active ingredient concentration of 25.5%.

Formulation Example 7 (A Flowable Concentrate)

1 part of Compound A, 0.1 part of Compound VI, 3 parts of polyoxyethylene sorbitan monooleate, 3 parts of CMC and 92.9 parts of water were mixed together and wet ground until the grain size of the active ingredients became 5$\mu$ or less to obtain a flowable concentrate of the present invention having an active ingredient concentration of 1.1%.

Formulation Example 8 (A Flowable Concentrate)

1 part of Compound A, 10 parts of Compound VII, 10 parts of Compound C, 3 parts of polyoxyethylene monooleate, 3 parts of CMC and 73 parts of water were mixed together and wet ground until the grain size of the active ingredients became 5$\mu$ or less to obtain a flowable concentrate of the present invention having an active ingredient concentration of 21%.

Formulation Example 9 (A Flowable Concentrate)

0.5 part of Compound A, 10 parts of Compound II, 10 parts of Compound C, 10 parts of Compound D, 3 parts of polyoxyethylene monooleate, 3 parts of CMC and 63.5 parts of water were mixed together and wet ground until the grain size of the active ingredients became 5$\mu$ or less to obtain a flowable concentrate of the present invention having an active ingredient concentration of 30.5%.

Formulation Example 10 (An Emulsifiable Concentrate)

1 part of Compound A, 2 parts of Compound III, 1.5 parts of imazalil, 3.5 parts of polyoxyethylene alkyl aryl ether (an emulsifying agent), 50 parts of cyclohexane and 42 parts of xylene were mixed together to obtain an emulsifiable concentrate of the present invention having an active ingredient concentration of 3%.

Formulation Example 11 (An Emulsifiable Concentrate)

1 part of Compound A, 4 parts of Compound IV, 4 parts of Compound C, 4 parts of hydroxyisoxazole, 15 parts of polyoxyethylene alkyl aryl ether (an emulsifying agent), 52 parts of cyclohexane and 20 parts of xylene were mixed together to obtain an emulsifiable concentrate of the present invention having an active ingredient concentration of 9%.

Formulation Example 12 (An Emulsifiable Concentrate)

0.5 part of Compound A, 4 parts of Compound VII, 2 parts of Compound C, 15 parts of polyoxyethylene alkyl aryl ether (an emulsifying agent), 50 parts of cyclohexane and 28.5 parts of xylene were mixed together to obtain an emulsifiable concentrate of the present invention having an active ingredient concentration of 10.5%.

TEST EXAMPLE 1

10 g of wheat seeds (variety: Norin No. 61) inoculated and infected with *Tilletia caries* were dipped into an aqueous solution containing a prescribed concentration of each of wettable powders of the present invention prepared in the same manner as in Formulation Examples 4 to 6, for 24 hours. Thereafter, they were shown in an upland field and cultivated on.

When the wheat came into ears, they were examined whether they had any symptoms of the disease or not, and the percentage of healthy seedlings was calculated from the following equation.

$$\text{Percentage of healthy seedlings} = \frac{\text{Number of healthy seedlings in treated plot}}{\text{Number of healthy seedlings in uninoculated and untreated plot}} \times 100$$

Moreover, the synergistic effect of the seed disinfectant composition of the present invention was studied according to the following procedure.

The effect (E) expected from the mixing of a compound X with another compound Y is generally given by the following equation:

$$E = m + n - \frac{m \cdot n}{100}$$

E: Preventing effect (%) (percentage of healthy seedlings) expected when a mixture of X and Y in respective amounts of p and q is used.
m: Preventing effect (%) (percentage of healthy seedlings) when X is used alone in an amount of p.
n: Preventing effect (%) (percentage of healthy seedlings) when Y is used alone in an amount of q.

The effect (E') expected from the mixing of a compound X', a compound Y' and a compound Z' is generally given by the following equation:

$$E' = m' + n' + l' - \frac{m' \cdot n' + n' \cdot l' + l' \cdot m'}{100} + \frac{m' \cdot n' \cdot l'}{10,000}$$

E': Preventing effect (%) (percentage of healthy seedlings) expected when a mixture of X', Y' and Z' in respective amounts of p', q' and r' is used.
m': Preventing effect (%) (percentage of healthy seedlings) when X' is used alone in an amount of p'.
n': Preventing effect (%) (percentage of healthy seedlings) when Y' is used alone in an amount of q'.
l': Preventing effect (%) (percentage of healthy seedlings) when Z' is used alone in an amount of r'.

An equation giving the effect expected from the mixing of four compounds can be introduced from the above equation. Needless to say, when any one of four compounds shows no preventing effect, the effect equals that expected from the mixing of other three compounds [See "Weeds" 15, pp. 20-2 (1967)].

If the found effect obtained by mixing the two is larger than the expected one, it can be said that a synergistic effect is obtained. The results are shown in Table 1.

TABLE 1

| | | | 1 | 2 | 3 | 4 | 5 | 6 | 7 | 8 | 9 | 10 | 11 | 12 |
|---|---|---|---|---|---|---|---|---|---|---|---|---|---|---|
| Concentration of Active Ingredients (ppm) | Compound A | | 0.5 | 0.5 | 0.5 | 0.5 | 0.5 | 0.5 | 0.5 | 0.5 | 0.5 | 0.5 | 0.5 | 0.5 |
| | Compound B | I | 5 | 5 | 5 | | | | | | | | | |
| | | II | | | | 5 | 5 | 5 | | | | | | |
| | | III | | | | | | | 5 | 5 | 5 | | | |
| | | IV | | | | | | | | | | 5 | | |
| | | V | | | | | | | | | | | 5 | |
| | | VI | | | | | | | | | | | | 5 |
| | | VII | | | | | | | | | | | | |
| | Compound C | | | | | | | | | | | | | |
| | Compound D | | | | | | | | | | | | | |
| (−)-Enantiomer Content in Compound A (% by weight) | | | 66.5 | 90.2 | 94.7 | 66.5 | 90.2 | 94.7 | 66.5 | 90.2 | 94.7 | 66.5 | 66.5 | 66.5 |
| Percentage of Healthy Seedlings | Found | | 80 | 83 | 85 | 81 | 84 | 86 | 79 | 82 | 83 | 80 | 78 | 77 |
| | Expected | | 47 | 52 | 54 | 44 | 49 | 52 | 47 | 52 | 55 | 45 | 47 | 45 |

| | | | 13 | 14 | 15 | 16 | 17 | 18 | 19 | 20 | 21 | 22 | 23 | 24 |
|---|---|---|---|---|---|---|---|---|---|---|---|---|---|---|
| Concentration of Active Ingredients (ppm) | Compound A | | 0.5 | 0.5 | 0.5 | 0.5 | 0.5 | 0.5 | 0.5 | 0.5 | 0.5 | 0.5 | 0.5 | 0.5 |
| | Compound B | I | | | | 5 | | | | | | | | |
| | | II | | | | | 5 | 5 | 5 | | | | | |
| | | III | | | | | | | | 5 | | | | |
| | | IV | | | | | | | | | 5 | | | |
| | | V | | | | | | | | | | 5 | | |
| | | VI | | | | | | | | | | | 5 | |
| | | VII | 5 | 5 | 5 | | | | | | | | | 5 |
| | Compound C | | | | | 5 | 5 | 5 | 5 | 5 | 5 | 5 | 5 | 5 |
| | Compound D | | | | | | | | | | | | | |
| (−)-Enantiomer Content in Compound A (% by weight) | | | 66.5 | 90.2 | 94.7 | 66.5 | 66.5 | 90.2 | 94.7 | 66.5 | 66.5 | 66.5 | 66.5 | 66.5 |
| Percentage of Healthy Seedlings | Found | | 82 | 84 | 85 | 91 | 90 | 96 | 99 | 91 | 90 | 92 | 91 | 90 |
| | Expected | | 47 | 52 | 54 | 52 | 50 | 54 | 57 | 53 | 51 | 52 | 51 | 52 |

| | | | 25 | 26 | 27 | 28 | 29 | 30 | 31 | 32 | 33 | 34 | 35 |
|---|---|---|---|---|---|---|---|---|---|---|---|---|---|
| Concentration of Active Ingredients (ppm) | Compound A | | 0.5 | 0.5 | 0.5 | 0.5 | 0.5 | 0.5 | 0.5 | 0.5 | 0.5 | 0.5 | 0.5 |
| | Compound B | I | | 5 | | | | | | | | | |
| | | II | | | | 5 | 5 | 5 | | | | | |
| | | III | | | | | | | 5 | 5 | 5 | | |

TABLE 1-continued

|  |  |  |  |  |  |  |  |  |  |  |  |
|---|---|---|---|---|---|---|---|---|---|---|---|
|  |  | IV |  |  |  |  |  |  |  | 5 |  |  |
|  |  | V |  |  |  |  |  |  |  |  |  | 5 |
|  |  | VII | 5 |  |  |  |  |  |  |  |  |  |
|  | Compound C |  | 5 | 5 | 5 | 5 | 5 | 5 | 5 | 5 | 5 | 5 | 5 |
|  | Compound D |  |  |  | 1 | 1 | 1 | 1 | 1 | 1 | 1 | 1 | 1 |
| (−)-Enantiomer Content in Compound A (% by weight) |  |  | 90.2 | 94.7 | 66.5 | 66.5 | 90.2 | 94.7 | 66.5 | 90.2 | 94.7 | 66.5 | 66.5 |
| Percentage of | Found |  | 9.3 | 98 | 95 | 94 | 99 | 100 | 94 | 98 | 100 | 94 | 95 |
| Healthy Seedlings | Expected |  | 56 | 59 | 52 | 50 | 54 | 57 | 53 | 57 | 59 | 51 | 52 |

|  |  |  | 36 | 37 | 38 | 39 | 40 | 41 | 42 | 43 | 44 | 45 |
|---|---|---|---|---|---|---|---|---|---|---|---|---|
| Concentration | Compound A |  | 0.5 | 0.5 | 0.5 | 0.5 | 11.5 | 0.5 | 11.5 | 0.5 | 11.5 | 0.5 |
| of | Compound B | I |  |  |  |  |  |  |  |  |  |  |
| Active Ingredients |  | II |  |  |  |  |  |  |  |  |  |  |
| (ppm) |  | III |  |  |  |  |  |  |  |  |  |  |
|  |  | IV |  |  |  |  |  |  |  |  |  |  |
|  |  | V |  |  |  |  |  |  |  |  |  |  |
|  |  | VI | 5 |  |  |  |  |  |  |  |  |  |
|  |  | VII |  | 5 | 5 | 5 |  |  |  |  |  |  |
|  | Comound C |  | 5 | 5 | 5 | 5 |  |  |  |  |  |  |
|  | Compound D |  | 1 | 1 | 1 | 1 |  |  |  |  |  |  |
| (−)-Enantiomer Content in Compound A (% by weight) |  |  | 66.5 | 66.5 | 90.2 | 94.7 | 66.5 | 66.5 | 90.2 | 90.2 | 94.7 | 94.7 |
| Percentage of | Found |  | 93 | 95 | 98 | 100 | 70 | 35 | 82 | 41 | 85 | 44 |
| Healthy Seedlings | Expected |  | 51 | 52 | 56 | 59 | — | — | — | — | — | — |

|  |  |  | 46 | 47 | 48 | 49 | 50 | 51 | 52 | 53 | 54 | 55 |
|---|---|---|---|---|---|---|---|---|---|---|---|---|
| Concentraction | Compound A |  |  |  |  |  |  |  |  |  |  |  |
| of | Compound B | I | 11.5 | 5 |  |  |  |  |  |  |  |  |
| Active Ingredients |  | II |  |  | 11.5 | 5 |  |  |  |  |  |  |
| (ppm) |  | III |  |  |  |  | 11.5 | 5 |  |  |  |  |
|  |  | IV |  |  |  |  |  |  | 11.5 | 5 |  |  |
|  |  | V |  |  |  |  |  |  |  |  | 11.5 | 5 |
|  |  | VI |  |  |  |  |  |  |  |  |  |  |
|  |  | VII |  |  |  |  |  |  |  |  |  |  |
|  | Compound C |  |  |  |  |  |  |  |  |  |  |  |
|  | Compound D |  |  |  |  |  |  |  |  |  |  |  |
| (−)-Enantiomer Content in Compound A (% by weight) |  |  | — | — | — |  |  |  |  |  |  |  |
| Percentage of | Found |  | 23 | 18 | 20 | 14 | 21 | 19 | 23 | 16 | 20 | 18 |
| Healthy Seedlings | Expected |  | — | — | — |  |  |  |  |  |  |  |

|  |  |  | 56 | 57 | 58 | 59 | 60 | 61 | 62 | 63 | 0* | 00** |
|---|---|---|---|---|---|---|---|---|---|---|---|---|
| Concentration | Compound A |  |  |  |  |  |  |  |  |  |  |  |
| of | Compound B | I |  |  |  |  |  |  |  |  |  |  |
| Active Ingredients |  | II |  |  |  |  |  |  |  |  |  |  |
| (ppm) |  | III |  |  |  |  |  |  |  |  |  |  |
|  |  | IV |  |  |  |  |  |  |  |  |  |  |
|  |  | V |  |  |  |  |  |  |  |  |  |  |
|  |  | VI | 11.5 | 5 |  |  |  |  |  |  |  |  |
|  |  | VII |  |  | 11.5 | 5 |  |  |  |  |  |  |
|  | Compound C |  |  |  |  |  | 11.5 | 5 |  |  |  |  |
|  | Compound D |  |  |  |  |  |  |  | 11.5 | 5 |  |  |
| (−)-Enantiomer Content in Compound A (% by weight) |  |  |  |  |  |  |  |  |  |  |  |  |
| Percentage of | Found |  | 18 | 16 | 22 | 18 | 18 | 10 | 0 | 0 | 0 | 100 |
| Healthy Seedlings | Expected |  |  |  |  |  |  |  |  |  |  |  |

*Inoculation and no treatment
**No inoculation and no treatment

Test Example 2

Each of flowable concentrates of the seed disinfectant composition of the present invention prepared according to Formulation Examples 7 to 9 was sprayed onto 10 g of barley seeds (variety: New Golden) infected with *Helminthosporium gramineum*. Thereafter, the barley seeds were sown in an upland field and cultivated on. When the barley came into ears, they were examined whether they had any symptoms of the disease or not; percentage of healthy seedlings was calculated in the same manner as in Test Example 1 and a synergistic effect was confirmed by comparing the found value with the expected value. The results are shown in Table 2.

TABLE 2

|  |  |  | 1 | 2 | 3 | 4 | 5 | 6 | 7 | 8 | 9 | 10 |
|---|---|---|---|---|---|---|---|---|---|---|---|---|
| Amount of | Compound A |  | 1 | 1 | 1 | 1 | 1 | 1 | 1 | 1 | 1 | 1 |
| Active Ingredients | Compound B | I | 5 | 5 | 6 |  |  |  |  |  |  |  |
| (g/100 kg-dry seed) |  | II |  |  |  | 5 | 5 | 5 |  |  |  |  |
|  |  | III |  |  |  |  |  |  | 5 | 5 | 5 |  |
|  |  | IV |  |  |  |  |  |  |  |  |  | 5 |
|  |  | V |  |  |  |  |  |  |  |  |  |  |
|  |  | VI |  |  |  |  |  |  |  |  |  |  |
|  |  | VII |  |  |  |  |  |  |  |  |  |  |
|  | Compound C |  |  |  |  |  |  |  |  |  |  |  |
|  | Compound D |  |  |  |  |  |  |  |  |  |  |  |
| (−)-Enantiomer Content in Compound A (% by weight) |  |  | 66.5 | 90.2 | 94.7 | 66.5 | 90.2 | 94.7 | 66.5 | 90.2 | 94.7 | 66.5 |
| Percentage of | Found |  | 81 | 85 | 87 | 80 | 83 | 85 | 82 | 87 | 88 | 79 |

TABLE 2-continued

| Healthy Seedlings | Expected | | 32 | 42 | 48 | 32 | 42 | 48 | 32 | 42 | 48 | 32 |
|---|---|---|---|---|---|---|---|---|---|---|---|---|
| | | | 11 | 12 | 13 | 14 | 15 | 16 | 17 | 18 | 19 | 20 |
| Amount of Active Ingredients (g/100 kg-dry seed) | Compound A | | 1 | 1 | 1 | 1 | 1 | 1 | 1 | 1 | 1 | 1 |
| | Compound B | I | | | | | | | 5 | | | |
| | | II | | | | | | | | 5 | 5 | 5 |
| | | III | | | | | | | | | | 5 |
| | | IV | | | | | | | | | | |
| | | V | 5 | | | | | | | | | |
| | | VI | | 5 | | | | | | | | |
| | | VII | | | 5 | 5 | 5 | | | | | |
| | Compound C | | | | | | | | 5 | 5 | 5 | 5 | 5 |
| | Compound D | | | | | | | | | | | |
| (−)-Enantiomer Content in Compound A (% by weight) | | | 66.5 | 66.5 | 66.5 | 90.2 | 94.7 | 66.5 | 66.5 | 90.2 | 94.7 | 66.5 |
| Percentage of Healthy Seedlings | Found | | 79 | 77 | 81 | 86 | 89 | 88 | 90 | 96 | 98 | 89 |
| | Expected | | 32 | 32 | 32 | 42 | 48 | 42 | 42 | 50 | 55 | 42 |
| | | | 21 | 22 | 23 | 24 | 25 | 26 | 27 | 28 | 29 | 30 |
| Amount of Active Ingredients (g/100 kg-dry seed) | Compound A | | 1 | 1 | 1 | 1 | 1 | 1 | 1 | 1 | 1 | 1 |
| | Compound B | I | | | | | | | 5 | | | |
| | | II | | | | | | | | 5 | 5 | 5 |
| | | III | | | | | | | | | | |
| | | IV | 5 | | | | | | | | | |
| | | V | | 5 | | | | | | | | |
| | | VI | | | 5 | | | | | | | |
| | | VII | | | | 5 | 5 | 5 | | | | |
| | Compound C | | 5 | 5 | 5 | 5 | 5 | 5 | 5 | 5 | 5 | 5 |
| | Compound D | | | | | | | | 5 | 5 | 5 | 5 |
| (−)-Enantiomer Content in Compound A (% by weight) | | | 66.5 | 66.5 | 66.5 | 66.5 | 90.2 | 94.7 | 66.5 | 66.5 | 90.2 | 94.7 |
| Percentage of Healthy Seedlings | Found | | 87 | 89 | 86 | 88 | 93 | 96 | 93 | 96 | 99 | 100 |
| | Expected | | 42 | 42 | 42 | 42 | 50 | 55 | 42 | 42 | 50 | 55 |
| | | | 31 | 32 | 33 | 34 | 35 | 36 | 37 | 38 | 39 | |
| Amount of Active Ingredients (g/100 kg-dry seed) | Compound A | | 1 | 1 | 1 | 1 | 1 | 1 | 1 | 1 | | |
| | Compound B | I | | | | | | | | | | |
| | | II | | | | | | | | | | |
| | | III | 5 | 5 | 5 | | | | | | | |
| | | IV | | | | 5 | | | | | | |
| | | V | | | | | 5 | | | | | |
| | | VI | | | | | | 5 | | | | |
| | | VII | | | | | | | 5 | 5 | 5 | |
| | Compound C | | 5 | 5 | 5 | 5 | 5 | 5 | 5 | 5 | 5 | |
| | Compound D | | 5 | 5 | 5 | 5 | 5 | 5 | 5 | 5 | 5 | |
| (−)-Enantiomer Content in Compound A (% by weight) | | | 66.5 | 90.2 | 94.7 | 66.5 | 66.5 | 66.5 | 66.5 | 90.2 | 94.7 | |
| Percentage of Healthy Seedlings | Found | | 92 | 97 | 100 | 91 | 92 | 90 | 93 | 98 | 100 | |
| | Expected | | 42 | 50 | 55 | 42 | 42 | 42 | 42 | 50 | 55 | |
| | | | 40 | 41 | 42 | 43 | 44 | 45 | 46 | 47 | 48 | 49 | 50 |
| Amount of Active Ingredients (g/100 kg-dry seed) | Compound A | | 16 | 1 | 16 | 1 | 16 | 1 | | | | | |
| | Compound B | I | | | | | | | 16 | 5 | | | |
| | | II | | | | | | | | 16 | 5 | | |
| | | III | | | | | | | | | | | 16 |
| | | IV | | | | | | | | | | | |
| | | V | | | | | | | | | | | |
| | | VI | | | | | | | | | | | |
| | | VII | | | | | | | | | | | |
| | Compound C | | | | | | | | | | | | |
| | Compound D | | | | | | | | | | | | |
| (−)-Enantiomer Content in Compound A (% by weight) | | | 66.5 | 66.5 | 90.2 | 90.2 | 94.7 | 94.7 | | | | | |
| Percentage of Healthy Seedlings | Found | | 72 | 32 | 98 | 42 | 100 | 48 | 0 | 0 | 0 | 0 | 0 |
| | Expected | | | | | | | | | | | | |
| | | | 51 | 52 | 53 | 54 | 55 | 56 | 57 | 58 | 59 | 60 | 61 | 62 | 63 | 0* | 00** |
| Amount of Active Ingredients (g/100 kg-dry seed) | Compound A | | | | | | | | | | | | | | | | |
| | Compound B | I | | | | | | | | | | | | | | | |
| | | II | | | | | | | | | | | | | | | |
| | | III | 5 | | | | | | | | | | | | | | |
| | | IV | | 16 | 5 | | | | | | | | | | | | |
| | | V | | | | 16 | 5 | | | | | | | | | | |
| | | VI | | | | | | 16 | 5 | | | | | | | | |
| | | VII | | | | | | | | 16 | 5 | | | | | | |
| | Compound C | | | | | | | | | | | 16 | 5 | | | | |
| | Compound D | | | | | | | | | | | | | 16 | 5 | | |
| (−)-Enantiomer Content in Compound A (% by weight) | | | | | | | | | | | | | | | | | |
| Percentage of Healthy Seedlings | Found | | 0 | 0 | 0 | 0 | 0 | 0 | 0 | 0 | 0 | 35 | 14 | 0 | 0 | 0 | 100 |
| | Expected | | | | | | | | | | | | | | | | |

*Inoculation and no treatment
**No inoculation and no treatment

Test Example 3

Each of emulsifiable concentrates of the seed disinfectant composition of the present invention prepared according to Formulation Examples 10 to 12 was sprayed onto 10 g of barley seeds (variety: Video) infected with *Ustilago nuda*. Thereafter, the barley seeds were sown in an upland field and cultivated on. When the barley came into ears, they were examined whether they had any symptoms of the disease or not, percentage of healthy seedlings was calculated in the same manner as in Test Example 1 and a synergistic effect was confirmed by comparing the found value with the expected value. The results are shown in Table 3.

TABLE 3

|  |  |  | 1 | 2 | 3 | 4 | 5 | 6 | 7 | 8 | 9 | 10 | 11 | 12 |
|---|---|---|---|---|---|---|---|---|---|---|---|---|---|---|
| Amount of Active Ingredients (g/100 kg-dry seed) | Compound A | | 0.5 | 0.5 | 0.5 | 0.5 | 0.5 | 0.5 | 0.5 | 0.5 | 0.5 | 0.5 | 0.5 | 0.5 |
| | Compound B | I | 10 | 10 | 10 | | | | | | | | | |
| | | II | | | | 10 | 10 | 10 | | | | | | |
| | | III | | | | | | | 10 | 10 | 10 | | | |
| | | IV | | | | | | | | | | 10 | | |
| | | V | | | | | | | | | | | 10 | |
| | | VI | | | | | | | | | | | | 10 |
| | | VII | | | | | | | | | | | | |
| | Compound C | | | | | | | | | | | | | |
| | Compound D | | | | | | | | | | | | | |
| (−)-Enantiomer Content in Compound A (% by weight) | | | 66.5 | 90.2 | 94.7 | 66.5 | 90.2 | 94.7 | 66.5 | 90.2 | 94.7 | 66.5 | 66.5 | 66.5 |
| Percentage of Healthy Seedlings | Found | | 82 | 87 | 90 | 83 | 88 | 90 | 81 | 86 | 89 | 79 | 79 | 78 |
| | Expected | | 66 | 75 | 76 | 66 | 75 | 77 | 65 | 74 | 76 | 65 | 65 | 64 |
|  |  |  | 13 | 14 | 15 | 16 | 17 | 18 | 19 | 20 | 21 | 22 | 23 | 24 |
| Amount of Active Ingredients (g/100 kg-dry seed) | Compound A | | 0.5 | 0.5 | 0.5 | 0.5 | 0.5 | 0.5 | 0.5 | 0.5 | 0.5 | 0.5 | 0.5 | 0.5 |
| | Compound B | I | | | | 10 | | | | | | | | |
| | | II | | | | | 10 | 10 | 10 | | | | | |
| | | III | | | | | | | | 10 | | | | |
| | | IV | | | | | | | | | 10 | | | |
| | | V | | | | | | | | | | 10 | | |
| | | VI | | | | | | | | | | | 10 | |
| | | VII | 10 | 10 | 10 | | | | | | | | | 10 |
| | Compound C | | | | | 10 | 10 | 10 | 10 | 10 | 10 | 10 | 10 | 10 |
| | Compound D | | | | | | | | | | | | | |
| (−)-Enantiomer Content in Compound A (% by weight) | | | 66.5 | 90.2 | 94.7 | 66.5 | 66.5 | 90.2 | 94.7 | 66.5 | 66.5 | 66.5 | 66.5 | 66.5 |
| Percentage of Healthy Seedlings | Found | | 81 | 87 | 91 | 88 | 89 | 93 | 96 | 85 | 84 | 85 | 83 | 87 |
| | Expected | | 67 | 76 | 77 | 66 | 66 | 75 | 77 | 65 | 65 | 65 | 64 | 67 |
|  |  |  | 25 | 26 | 27 | 28 | 29 | 30 | 31 | 32 | 33 | 34 | 35 | 36 |
| Amount of Active Ingredients (g/100 kg-dry seed) | Compound A | | 0.5 | 0.5 | 30.5 | 0.5 | 30.5 | 0.5 | 30.5 | 0.5 | | | | |
| | Compound B | I | | | | | | | | | 30.5 | 10 | | |
| | | II | | | | | | | | | | | 30.5 | 10 |
| | | III | | | | | | | | | | | | |
| | | IV | | | | | | | | | | | | |
| | | V | | | | | | | | | | | | |
| | | VI | | | | | | | | | | | | |
| | | VII | 10 | 10 | | | | | | | | | | |
| | Compound C | | 10 | 10 | | | | | | | | | | |
| | Compound D | | | | | | | | | | | | | |
| (−)-Enantiomer Content in Compound A (% by weight) | | | 90.2 | 94.7 | 66.5 | 66.5 | 90.2 | 90.2 | 94.7 | 94.7 | | | | |
| Percentage of Healthy Seedlings | Found | | 92 | 96 | 100 | 58 | 100 | 69 | 100 | 71 | 25 | 18 | 28 | 20 |
| | Expected | | 76 | 77 | | | | | | | | | | |
|  |  |  | 37 | 38 | 39 | 40 | 41 | 42 | 43 | 44 | 45 | 46 | 47 | 48 |
| Amount of Active Ingredients (g/100 kg-dry seed) | Compound A | | | | | | | | | | | | | |
| | Compound B | I | | | | | | | | | | | | |
| | | II | | | | | | | | | | | | |
| | | III | 30.5 | 10 | | | | | | | | | | |
| | | IV | | | 30.5 | 10 | | | | | | | | |
| | | V | | | | | 30.5 | 10 | | | | | | |
| | | VI | | | | | | | 30.5 | 10 | | | | |
| | | VII | | | | | | | | | 30.5 | 10 | | |
| | Compound C | | | | | | | | | | | | 30.5 | 10 |
| | Compound D | | | | | | | | | | | | | |
| (−)-Enantiomer Content in Compound A (% by weight) | | | | | | | | | | | | | | |
| Percentage of Healthy Seedlings | Found | | 23 | 16 | 24 | 17 | 24 | 16 | 19 | 15 | 25 | 21 | 5 | 0 |
| | Expected | | | | | | | | | | | | | |
|  |  |  |  |  |  |  |  |  |  |  |  |  | 0* | 00* |
| Amount of Active Ingredients (g/100 kg-dry seed) | Compound A | | | | | | | | | | | | | |
| | Compound B | I | | | | | | | | | | | | |
| | | II | | | | | | | | | | | | |
| | | III | | | | | | | | | | | | |
| | | IV | | | | | | | | | | | | |
| | | V | | | | | | | | | | | | |
| | | VI | | | | | | | | | | | | |
| | | VII | | | | | | | | | | | | |
| | Compound C | | | | | | | | | | | | | |
| | Compound D | | | | | | | | | | | | | |
| (−)-Enantiomer Content in Compound A (% by weight) | | | | | | | | | | | | | | |
| Percentage of | Found | | | | | | | | | | | | 0 | 100 |

TABLE 3-continued

| | Healthy Seedlings | Expected |
|---|---|---|

*Inoculation and no treatment
**No inoculation and no treatment

Test Example 4

10 g of wheat seeds (variety: Norin No. 73) infected with *Fusarium nivale* was dust-coated with each of wettable powders of the present invention prepared in the same manner as in Formulation Examples 4 and 5. Thereafter, the wheat seeds were sown in an upland field and cultivated on. When the wheat reached the fourth leafing stage, they were examined whether they had any symptoms of the disease or not, precentage of healthy seedlings was calculated in the same manner as in Test Example 1. The results are shown in Table 4.

TABLE 4

| | | | 1 | 2 | 3 | 4 | 5 | 6 | 7 | 8 | 9 | 10 | 11 |
|---|---|---|---|---|---|---|---|---|---|---|---|---|---|
| Amount of | Compound A | | 10 | 10 | 10 | 10 | 10 | 10 | 10 | 10 | 10 | 10 | 10 |
| Active Ingredients | Compound B | I | 0.5 | 0.5 | 0.5 | | | | | | | | |
| (g/100 kg-dry seed) | | II | | | | 0.5 | 0.5 | 0.5 | | | | | |
| | | III | | | | | | | 0.5 | 0.5 | 0.5 | | |
| | | IV | | | | | | | | | | 0.5 | |
| | | V | | | | | | | | | | | 0.5 |
| | | VI | | | | | | | | | | | |
| | | VII | | | | | | | | | | | |
| | Compound C | | | | | | | | | | | | |
| | Compound D | | | | | | | | | | | | |
| (−)-Enantiomer Content in Compound A (% by weight) | | | 66.5 | 90.2 | 94.7 | 66.5 | 90.2 | 94.7 | 66.5 | 90.2 | 94.7 | 66.5 | 66.5 |
| Percentage of | Found | | 83 | 88 | 90 | 82 | 87 | 90 | 81 | 86 | 89 | 82 | 81 |
| Healthy Seedlings | Expected | | 51 | 57 | 60 | 52 | 58 | 61 | 50 | 55 | 59 | 50 | 50 |

| | | | 12 | 13 | 14 | 15 | 16 | 17 | 18 | 19 | 20 | 21 | 22 |
|---|---|---|---|---|---|---|---|---|---|---|---|---|---|
| Amount of | Compound A | | 10 | 10 | 10 | 10 | 10 | 10 | 10 | 10 | 10 | 10 | 10 |
| Active Ingredients | Compound B | I | | | | | 0.5 | | | | | | |
| (g/100 kg-dry seed) | | II | | | | | | | 0.5 | 0.5 | 0.5 | | |
| | | III | | | | | | | | | | 0.5 | |
| | | IV | | | | | | | | | | | 0.5 |
| | | V | | | | | | | | | | | 0.5 |
| | | VI | 0.5 | | | | | | | | | | |
| | | VII | | 0.5 | 0.5 | 0.5 | | | | | | | |
| | Compound C | | | | | | 1 | 1 | 1 | 1 | 1 | 1 | 1 |
| | Compound D | | | | | | | | | | | | |
| (−)-Enantiomer Content in Compound A (% by weight) | | | 66.5 | 66.5 | 90.2 | 94.7 | 66.5 | 66.5 | 90.2 | 94.7 | 66.5 | 66.5 | 66.5 |
| Percentage of | Found | | 80 | 83 | 88 | 91 | 88 | 92 | 96 | 98 | 87 | 87 | 86 |
| Healthy Seedlings | Expected | | 49 | 54 | 59 | 62 | 53 | 55 | 60 | 63 | 52 | 53 | 52 |

| | | | 23 | 24 | 25 | 26 | 27 | 28 | 29 | 30 | 31 | 32 | 33 |
|---|---|---|---|---|---|---|---|---|---|---|---|---|---|
| Amount of | Compound A | | 10 | 10 | 10 | 10 | 10 | 10 | 10 | 10 | 10 | 10 | 10 |
| Active Ingredients | Compound B | I | | | | | 0.5 | | | | | | |
| (g/100 kg-dry seed) | | II | | | | | | | 0.5 | 0.5 | 0.5 | | |
| | | III | | | | | | | | | | 0.5 | 0.5 | 0.5 |
| | | IV | | | | | | | | | | | |
| | | V | | | | | | | | | | | |
| | | VI | 0.5 | | | | | | | | | | |
| | | VII | | 0.5 | 0.5 | 0.5 | | | | | | | |
| | Compound C | | 1 | 1 | 1 | 1 | 1 | 1 | 1 | 1 | 1 | 1 | 1 |
| | Compound D | | | | | | 1 | 1 | 1 | 1 | 1 | 1 | 1 |
| (−)-Enantiomer Content in Compound A (% by weight) | | | 66.5 | 66.5 | 90.2 | 94.7 | 66.5 | 66.5 | 90.2 | 94.7 | 66.5 | 90.2 | 94.7 |
| Percentage of | Found | | 85 | 87 | 94 | 96 | 94 | 96 | 98 | 100 | 93 | 99 | 100 |
| Healthy Seedlings | Expected | | 51 | 56 | 61 | 64 | 53 | 55 | 60 | 63 | 52 | 58 | 61 |

| | | | 34 | 35 | 36 | 37 | 38 | 39 | 40 | 41 | 42 | 43 | 44 |
|---|---|---|---|---|---|---|---|---|---|---|---|---|---|
| Amount of | Compound A | | 10 | 10 | 10 | 10 | 10 | 10 | 12.5 | 10 | 12.5 | 10 | 12.5 |
| Active Ingredients | Compound B | I | | | | | | | | | | | |
| (g/100 kg-dry seed) | | II | | | | | | | | | | | |
| | | III | | | | | | | | | | | |
| | | IV | 0.5 | | | | | | | | | | |
| | | V | | 0.5 | | | | | | | | | |
| | | VI | | | 0.5 | | | | | | | | |
| | | VII | | | | 0.5 | 0.5 | 0.5 | | | | | |
| | Compound C | | 1 | 1 | 1 | 1 | 1 | 1 | | | | | |
| | Compound D | | 1 | 1 | 1 | 1 | 1 | 1 | | | | | |
| (−)-Enantiomer Content in Compound A (% by weight) | | | 66.5 | 66.5 | 66.5 | 66.5 | 90.2 | 94.7 | 66.5 | 66.5 | 90.2 | 90.2 | 94.7 |
| Percentage of | Found | | 94 | 93 | 90 | 94 | 99 | 100 | 41 | 38 | 48 | 45 | 52 |
| Healthy Seedlings | Expected | | 53 | 52 | 51 | 56 | 61 | 64 | | | | | |

| | | | 45 | 46 | 47 | 48 | 49 | 50 | 51 | 52 | 53 | 54 | 55 |
|---|---|---|---|---|---|---|---|---|---|---|---|---|---|
| Amount of | Compound A | | 10 | | | | | | | | | | |
| Active Ingredients | Compound B | I | | 12.5 | 0.5 | | | | | | | | |
| (g/100 kg-dry seed) | | II | | | | 12.5 | 0.5 | | | | | | |
| | | III | | | | | | 12.5 | 0.5 | | | | |
| | | IV | | | | | | | | 12.5 | 0.5 | | |
| | | V | | | | | | | | | | 12.5 | 0.5 |
| | | VI | | | | | | | | | | | |

TABLE 4-continued

|  |  |  |  |  |  |  |  |  |  |  |  |  |
|---|---|---|---|---|---|---|---|---|---|---|---|---|
|  | VII |  |  |  |  |  |  |  |  |  |  |  |
| Compound C |  |  |  |  |  |  |  |  |  |  |  |  |
| Compound D |  |  |  |  |  |  |  |  |  |  |  |  |
| (−)-Enantiomer Content in Compound A (% by weight) | 94.7 |  |  |  |  |  |  |  |  |  |  |  |
| Percentage of Found | 49 | 58 | 21 | 62 | 23 | 56 | 19 | 57 | 20 | 57 |  | 19 |
| Healthy Seedlings Expected |  |  |  |  |  |  |  |  |  |  |  |  |

|  |  | 56 | 57 | 58 | 59 | 60 | 61 | 62 | 63 | 0* | 00** |
|---|---|---|---|---|---|---|---|---|---|---|---|
| Amount of | Compound A |  |  |  |  |  |  |  |  |  |  |
| Active Ingredients | Compound B I |  |  |  |  |  |  |  |  |  |  |
| (g/100 kg-dry seed) | II |  |  |  |  |  |  |  |  |  |  |
|  | III |  |  |  |  |  |  |  |  |  |  |
|  | IV |  |  |  |  |  |  |  |  |  |  |
|  | V |  |  |  |  |  |  |  |  |  |  |
|  | VI | 12.5 | 0.5 |  |  |  |  |  |  |  |  |
|  | VII |  |  | 12.5 | 0.5 |  |  |  |  |  |  |
|  | Compound C |  |  |  |  | 12.5 | 1 |  |  |  |  |
|  | Compound D |  |  |  |  |  |  | 12.5 | 1 |  |  |
| (−)-Enantiomer Content in Compound A (% by weight) |  |  |  |  |  |  |  |  |  |  |  |
| Percentage of Found | 51 | 17 | 63 | 25 | 25 | 5 | 0 | 0 | 0 | 100 |
| Healthy Seedlings Expected |  |  |  |  |  |  |  |  |  |  |  |

*Inoculation and no treatment
**No inoculation and no treatment

Test Example 5

Each of emulsifiable concentrates of the present invention prepared according to Formulation Examples 10 to 12 was sprayed onto 10 g of barley seeds (variety: Sonja) infected with *Pyrenophora teres*. Thereafter, the barley seeds were sown in an upland field and cultivated on. When the barley came into ears, they were examined whether they had any symptoms of the disease or not, percentage of healthy seedlings was calculated in the same manner as in Test Example 1. The results are shown in Table 5.

TABLE 5

|  |  |  | 1 | 2 | 3 | 4 | 5 | 6 | 7 | 8 | 9 | 10 | 11 | 12 |
|---|---|---|---|---|---|---|---|---|---|---|---|---|---|---|
|  | Compound A |  | 10 | 10 | 10 | 10 | 10 | 10 | 10 | 10 | 10 | 10 | 10 | 10 |
| Amount of | Compound B | I | 0.5 | 0.5 | 0.5 |  |  |  |  |  |  |  |  |  |
| Active Ingredients |  | II |  |  |  | 0.5 | 0.5 | 0.5 |  |  |  |  |  |  |
| (g/100 kg-dry seed) |  | III |  |  |  |  |  |  | 0.5 | 0.5 | 0.5 |  |  |  |
|  |  | IV |  |  |  |  |  |  |  |  |  | 0.5 |  |  |
|  |  | V |  |  |  |  |  |  |  |  |  |  | 0.5 |  |
|  |  | VI |  |  |  |  |  |  |  |  |  |  |  | 0.5 |
|  |  | VII |  |  |  |  |  |  |  |  |  |  |  |  |
|  | Compound C |  |  |  |  |  |  |  |  |  |  |  |  |  |
|  | Compound D |  |  |  |  |  |  |  |  |  |  |  |  |  |
| (−)-Enantiomer Content in Compound A (% by weight) | 66.5 | 90.2 | 94.7 | 66.5 | 90.2 | 94.7 | 66.5 | 90.2 | 94.7 | 66.5 | 66.5 | 66.5 |
| Percentage of | Found |  | 86 | 90 | 93 | 85 | 89 | 90 | 83 | 88 | 92 | 81 | 80 | 80 |
| Healthy Seedlings | Expected |  | 65 | 70 | 73 | 65 | 70 | 73 | 65 | 70 | 73 | 65 | 65 | 65 |

|  |  |  | 13 | 14 | 15 | 16 | 17 | 18 | 19 | 20 | 21 | 22 | 23 | 24 |
|---|---|---|---|---|---|---|---|---|---|---|---|---|---|---|
|  | Compound A |  | 10 | 10 | 10 | 10 | 10 | 10 | 10 | 10 | 10 | 10 | 10 | 10 |
| Amount of | Compound B | I |  |  |  | 0.5 |  |  |  |  |  |  |  |  |
| Active Ingredients |  | II |  |  |  |  | 0.5 | 0.5 | 0.5 |  |  |  |  |  |
| (g/100 kg-dry seed) |  | III |  |  |  |  |  |  |  | 0.5 |  |  |  |  |
|  |  | IV |  |  |  |  |  |  |  |  | 0.5 |  |  |  |
|  |  | V |  |  |  |  |  |  |  |  |  | 0.5 |  |  |
|  |  | VI |  |  |  |  |  |  |  |  |  |  | 0.5 |  |
|  |  | VII | 0.5 | 0.5 | 0.5 |  |  |  |  |  |  |  |  | 0.5 |
|  | Compound C |  |  |  |  | 20 | 20 | 20 | 20 | 20 | 20 | 20 | 20 | 20 |
|  | Compound D |  |  |  |  |  |  |  |  |  |  |  |  |  |
| (−)-Enantiomer Content in Compound A (% by weight) | 66.5 | 90.2 | 94.7 | 66.5 | 66.5 | 90.2 | 94.7 | 66.5 | 66.5 | 66.5 | 66.5 | 66.5 |
| Percentage of | Found |  | 85 | 91 | 94 | 89 | 91 | 96 | 97 | 88 | 87 | 88 | 85 | 91 |
| Healthy Seedlings | Expected |  | 65 | 70 | 73 | 74 | 74 | 78 | 80 | 74 | 74 | 74 | 74 | 74 |

|  |  |  | 25 | 26 | 27 | 28 | 29 | 30 | 31 | 32 | 33 | 34 | 35 | 36 |
|---|---|---|---|---|---|---|---|---|---|---|---|---|---|---|
|  | Compound A |  | 10 | 10 | 35.5 | 10 | 35.5 | 10 | 35.5 | 10 |  |  |  |  |
| Amount of | Compound B | I |  |  |  |  |  |  |  |  | 35.5 | 0.5 |  |  |
| Active Ingredients |  | II |  |  |  |  |  |  |  |  |  |  | 35.5 | 0.5 |
| (g/100 kg-dry seed) |  | III |  |  |  |  |  |  |  |  |  |  |  |  |
|  |  | IV |  |  |  |  |  |  |  |  |  |  |  |  |
|  |  | V |  |  |  |  |  |  |  |  |  |  |  |  |
|  |  | VI |  |  |  |  |  |  |  |  |  |  |  |  |
|  |  | VII | 0.5 | 0.5 |  |  |  |  |  |  |  |  |  |  |
|  | Compound C |  | 20 | 20 |  |  |  |  |  |  |  |  |  |  |
|  | Compound D |  |  |  |  |  |  |  |  |  |  |  |  |  |
| (−)-Enantiomer Content in Compound A (% by weight) | 90.2 | 94.7 | 66.5 | 66.5 | 90.2 | 90.2 | 94.7 | 94.7 |  |  |  |  |
| Percentage of | Found |  | 98 | 99 | 100 | 65 | 100 | 70 | 100 | 73 | 5 | 0 | 3 | 0 |
| Healthy Seedlings | Expected |  | 78 | 80 |  |  |  |  |  |  |  |  |  |  |

|  |  |  | 37 | 38 | 39 | 40 | 41 | 42 | 43 | 44 | 45 | 46 | 47 | 48 | 0* | 00** |
|---|---|---|---|---|---|---|---|---|---|---|---|---|---|---|---|---|
| Amount of | Compound A |  |  |  |  |  |  |  |  |  |  |  |  |  |  |  |
|  | Compound B | I |  |  |  |  |  |  |  |  |  |  |  |  |  |  |

TABLE 5-continued

| Active Ingredients (g/100 kg-dry seed) | | II | | | | | | | | | | | | | |
|---|---|---|---|---|---|---|---|---|---|---|---|---|---|---|---|
| | | III | 35.5 | 0.5 | | | | | | | | | | | |
| | | IV | | | 35.5 | 0.5 | | | | | | | | | |
| | | V | | | | | 35.5 | 0.5 | | | | | | | |
| | | VI | | | | | | | 35.5 | 0.5 | | | | | |
| | | VII | | | | | | | | | 35.5 | 0.5 | | | |
| | Compound C | | | | | | | | | | | | 35.5 | 20 | |
| | Compound D | | | | | | | | | | | | | | |
| (−)-Enantiomer Content in Compound A (% by weight) | | | | | | | | | | | | | | | |
| Percentage of Healthy Seedlings | Found | | 2 | 0 | 3 | 0 | 1 | 0 | 4 | 0 | 5 | 0 | 32 | 25 | 0 | 100 |
| | Expected | | | | | | | | | | | | | | |

*Inoculation and no treatment
**No inoculation and no treatment

Test Example 6

Each of flowable concentrates of the present invention prepared according to Formulation Examples 7 to 9 was sprayed onto 10 g of barley seeds (variety: Akashinriki) infected with *Rhynchosporium secalis*. Thereafter, the seeds were sown in an upland field and cultivated on. When the barley reached the internode elongation stage, they were examined whether they had any symptoms of the disease or not, percentage of healthy seedlings was calculated in the same manner as in Test Example 1. The results are shown in Table 6.

TABLE 6

| | | | 1 | 2 | 3 | 4 | 5 | 6 | 7 | 8 | 9 | 10 | 11 | 12 |
|---|---|---|---|---|---|---|---|---|---|---|---|---|---|---|
| Amount of Active Ingredients (g/100 kg-dry seed) | Compound A | | 10 | 10 | 10 | 10 | 10 | 10 | 10 | 10 | 10 | 10 | 10 | 10 |
| | Compound B | I | 1 | 1 | 1 | | | | | | | | | |
| | | II | | | | 1 | 1 | 1 | | | | | | |
| | | III | | | | | | | 1 | 1 | 1 | | | |
| | | IV | | | | | | | | | | 1 | | |
| | | V | | | | | | | | | | | 1 | |
| | | VI | | | | | | | | | | | | 1 |
| | | VII | | | | | | | | | | | | |
| | Compound C | | | | | | | | | | | | | |
| | Compound D | | | | | | | | | | | | | |
| (−)-Enantiomer Content in Compound A (% by weight) | | | 66.5 | 90.2 | 94.7 | 66.5 | 90.2 | 94.7 | 66.5 | 90.2 | 94.7 | 66.5 | 66.5 | 66.5 |
| Percentage of Healthy Seedlings | Found | | 78 | 83 | 84 | 79 | 81 | 84 | 77 | 80 | 83 | 78 | 77 | 76 |
| | Expected | | 44 | 49 | 51 | 42 | 47 | 48 | 41 | 46 | 48 | 39 | 43 | 41 |

| | | | 13 | 14 | 15 | 16 | 17 | 18 | 19 | 20 | 21 | 22 | 23 | 24 |
|---|---|---|---|---|---|---|---|---|---|---|---|---|---|---|
| Amount of Active Ingredients (g/100 kg-dry seed) | Compound A | | 10 | 10 | 10 | 10 | 10 | 10 | 10 | 10 | 10 | 10 | 10 | 10 |
| | Compound B | I | | | | 1 | | | | | | | | |
| | | II | | | | | 1 | 1 | 1 | | | | | |
| | | III | | | | | | | | 1 | | | | |
| | | IV | | | | | | | | | 1 | | | |
| | | V | | | | | | | | | | 1 | | |
| | | VI | | | | | | | | | | | 1 | |
| | | VII | 1 | 1 | 1 | | | | | | | | | 1 |
| | Compound C | | | | | 10 | 10 | 10 | 10 | 10 | 10 | 10 | 10 | 10 |
| | Compound D | | | | | | | | | | | | | |
| (−)-Enantiomer Content in Compound A (% by weight) | | | 66.5 | 90.2 | 94.7 | 66.5 | 66.5 | 90.2 | 94.7 | 66.5 | | 66.5 | 66.5 | 66.5 |
| Percentage of Healthy Seedlings | Found | | 79 | 84 | 85 | 84 | 85 | 89 | 91 | 83 | 83 | 85 | 84 | 86 |
| | Expected | | 45 | 50 | 51 | 45 | 42 | 47 | 49 | 41 | 39 | 43 | 41 | 45 |

| | | | 25 | 26 | 27 | 28 | 29 | 30 | 31 | 82 | 33 | 34 | 35 |
|---|---|---|---|---|---|---|---|---|---|---|---|---|---|
| Amount of Active Ingredients (g/100 kg-dry-seed) | Compound A | | 10 | 10 | 10 | 10 | 10 | 10 | 10 | 10 | 10 | 10 | 10 |
| | Compound B | I | | | 1 | | | | | | | | |
| | | II | | | | 1 | 1 | 1 | | | | | |
| | | III | | | | | | | 1 | 1 | 1 | | |
| | | IV | | | | | | | | | | 1 | |
| | | V | | | | | | | | | | | 1 |
| | | VI | | | | | | | | | | | |
| | | VII | 1 | 1 | | | | | | | | | |
| | Compound C | | 10 | 10 | 10 | 10 | 10 | 10 | 10 | 10 | 10 | 10 | 10 |
| | Compound D | | | | | 5 | 5 | 5 | 5 | 5 | 5 | 5 | 5 |
| (−)-Enantiomer Content in Compound A (% by weight) | | | 90.2 | 94.7 | 66.5 | 66.5 | 90.2 | 94.7 | 66.5 | 90.2 | 94.7 | 66.5 | 66.5 |
| Percentage of Healthy Seedlings | Found | | 91 | 93 | 89 | 90 | 97 | 100 | 89 | 97 | 100 | 89 | 91 |
| | Expected | | 50 | 52 | 45 | 42 | 47 | 49 | 41 | 47 | 48 | 39 | 43 |

| | | | 36 | 37 | 38 | 39 | 40 | 41 | 42 | 43 | 44 | 45 | 46 | 47 | 48 |
|---|---|---|---|---|---|---|---|---|---|---|---|---|---|---|---|
| Amount of Active Ingredients (g/100 kg-dry seed) | Compound A | | 10 | 10 | 10 | 10 | 26 | 10 | 26 | 10 | 26 | 10 | | | |
| | Compound B | I | | | | | | | | | | | 26 | 1 | |
| | | II | | | | | | | | | | | | | 26 |
| | | III | | | | | | | | | | | | | |
| | | IV | | | | | | | | | | | | | |
| | | V | | | | | | | | | | | | | |
| | | VI | 1 | | | | | | | | | | | | |
| | | VII | | 1 | 1 | 1 | | | | | | | | | |
| | Compound C | | 10 | 10 | 10 | 10 | | | | | | | | | |
| | Compound D | | 5 | 5 | 5 | 5 | | | | | | | | | |
| (−)-Enantiomer Content in Compound A (% by weight) | | | 66.5 | 66.5 | 90.2 | 94.7 | 66.5 | 66.5 | 90.2 | 90.2 | 94.7 | 94.7 | | | |
| Percentage of Found | | | 88 | 92 | 99 | 100 | 61 | 32 | 65 | 38 | 66 | 40 | 68 | 18 | 65 |

TABLE 6-continued

| Healthy Seedlings | Expected | | 41 | 45 | 50 | 52 | | | | | | | | | | | | | |
|---|---|---|---|---|---|---|---|---|---|---|---|---|---|---|---|---|---|---|---|
| | | | 49 | 50 | 51 | 52 | 53 | 54 | 55 | 56 | 57 | 58 | 59 | 60 | 61 | 62 | 63 | 0* | 00** |
| Amount of Active Ingredients (g/100 kg-dry seed) | Compound A Compound B | I II III IV V VI VII | | 1 | 26 | 1 | 26 | 1 | 26 | 1 | 26 | 1 | 26 | 1 | | | | | |
| | Compound C Compound D | | | | | | | | | | | | | | 26 | 10 26 | 5 | | |
| (−)-Enantiomer Content in Compound A (% by weight) | | | 14 | 58 | 13 | 55 | 10 | 59 | 16 | 51 | 13 | 66 | 19 | 5 | 1 | 0 | 0 | 0 | 100 |
| Percentage of Healthy Seedlings | Found Expected | | | | | | | | | | | | | | | | | | | |

*Inoculation and no treatment
**No inoculation and no treatment

Test Example 7

Grams of unhulled rice (variety: Kinki No. 33) infected with benomyl-sensitive or benomyl-resistant *Gibberella fujikuroi* were dust-coated with a prescribed amount of a dust of the seed disinfectant composition of the present invention prepared according to Formulation Example 1 or a commercially available seed disinfectant (Benlate T ®). Thereafter, the unhulled rice was sown in sandy loam in a plastic pot at a rate of 100 grains per pot, covered with soil and cultivated for 16 days in a greenhouse. Then, the symptoms of the disease was examined and the percentage of healthy seedlings was calculated in the same manner as in Test Example 1. The results are shown in Table 7.

TABLE 7

| | | | 1 | 2 | 3 | 4 | 5 | 6 | 7 | 8 | 9 |
|---|---|---|---|---|---|---|---|---|---|---|---|
| Amount of Active Ingredients (g/100 kg-dry seed) | Compound A Compound B | I II III IV V VI VII | 1 10 | 1 10 | 1 10 | 1 10 | 1 10 | 1 10 | 1 10 | 1 10 | 1 10 |
| | Compound C Compound D Benlate T ®*1 | | | | | | | | | | |
| (−)-Enantiomer Content in Compound A (% by weight) | | | 66.5 | 90.2 | 94.7 | 66.5 | 90.2 | 94.7 | 66.5 | 90.2 | 66.5 |
| Percentage of Healthy Seedlings | a*2 b*3 | | 100 100 | 100 100 | 100 100 | 100 100 | 100 100 | 100 100 | 100 100 | 100 100 | 100 100 |
| | | | 10 | 11 | 12 | 13 | 14 | 15 | 16 | 17 | 18 |
| Amount of Active Ingredients (g/100 kg-dry seed) | Compound A Compound B | I II III IV V VI VII | 1 | 1 | 1 | 1 | 1 | 1 | 1 10 | 1 10 | 1 10 |
| | | IV V VI VII | 10 | 10 | 10 | 10 | 10 | 10 | | | |
| | Compound C Compound D Benlate T ®*1 | | | | | | | | 10 | 10 | 10 |
| (−)-Enantiomer Content in Compound A (% by weight) | | | 66.5 | 66.5 | 66.5 | 66.5 | 90.2 | 94.7 | 66.5 | 66.5 | 90.2 |
| Percentage of Healthy Seedlings | a*2 b*3 | | 100 100 | 100 100 | 100 100 | 100 100 | 100 100 | 100 100 | 100 100 | 100 100 | 100 100 |
| | | | 19 | 20 | 21 | 22 | 23 | 24 | 25 | 26 | 27 |
| Amount of Active Ingredients (g/100 kg-dry seed) | Compound A Compound B | I II III IV V VI VII | 1 | 1 | 1 | 1 | 1 | 1 | 1 | 1 | 1 10 |
| | | II III IV V VI VII | 10 | 10 | 10 | 10 | 10 | 10 10 | 10 | 10 | |
| | Compound C Compound D Benlate T ®*1 | | 10 | 10 | 10 | 10 | 10 | 10 | 10 | 10 | 10 5 |
| (−)-Enantiomer Content in Compound A (% by weight) | | | 94.7 | 66.5 | 66.5 | 66.5 | 66.5 | 66.5 | 90.2 | 94.7 | 66.5 |
| Percentage of Healthy Seedlings | a*2 b*3 | | 100 100 | 100 100 | 100 100 | 100 100 | 100 100 | 100 100 | 100 100 | 100 100 | 100 100 |
| | | | 28 | 29 | 30 | 31 | 32 | 33 | 34 | 35 | 36 |
| Amount of Active Ingredients | Compound A Compound B | I | 1 | 1 | 1 | 1 | 1 | 1 | 1 | 1 | 1 |

TABLE 7-continued

| | | | | | | | | | | | | |
|---|---|---|---|---|---|---|---|---|---|---|---|---|
| (g/100 kg-dry seed) | | II | 10 | 10 | 10 | | | | | | | |
| | | III | | | | 10 | 10 | 10 | | | | |
| | | IV | | | | | | | 10 | | | |
| | | V | | | | | | | | 10 | | |
| | | VI | | | | | | | | | 10 | |
| | | VII | | | | | | | | | | |
| | Compound C | | 10 | 10 | 10 | 10 | 10 | 10 | 10 | 10 | 10 | |
| | Compound D | | 5 | 5 | 5 | 5 | 5 | 5 | 5 | 5 | 5 | |
| | Benlate T ®*¹ | | | | | | | | | | | |
| (−)-Enantiomer Content in Compound A (% by weight) | | | 66.5 | 90.2 | 94.7 | 66.5 | 90.2 | 94.7 | 66.5 | 66.5 | 66.5 | |
| Percentage of | a*² | | 100 | 100 | 100 | 100 | 100 | 100 | 100 | 100 | 100 | |
| Healthy Seedlings | b*³ | | 100 | 100 | 100 | 100 | 100 | 100 | 100 | 100 | 100 | |

| | | | 37 | 38 | 39 | 40 | 41 | 42 | 43 | 44 | 45 | 46 | 47 |
|---|---|---|---|---|---|---|---|---|---|---|---|---|---|
| Amount of | Compound A | | 1 | 1 | 1 | 26 | 1 | 26 | 1 | 26 | 1 | | |
| Active Ingredients | Compound B | I | | | | | | | | | | 26 | 10 |
| (g/100 kg-dry seed) | | II | | | | | | | | | | | |
| | | III | | | | | | | | | | | |
| | | IV | | | | | | | | | | | |
| | | V | | | | | | | | | | | |
| | | VI | | | | | | | | | | | |
| | | VII | 10 | 10 | 10 | | | | | | | | |
| | Compound C | | 10 | 10 | 10 | | | | | | | | |
| | Compound D | | 5 | 5 | 5 | | | | | | | | |
| | Benlate T ®*¹ | | | | | | | | | | | | |
| (−)-Enantiomer Content in Compound A (% by weight) | | | 66.5 | 90.2 | 94.7 | 66.5 | 66.5 | 90.2 | 90.2 | 94.7 | 94.7 | | |
| Percentage of | a*² | | 100 | 100 | 100 | 93 | 38 | 96 | 45 | 98 | 49 | 95 | 45 |
| Healthy Seedlings | b*³ | | 100 | 100 | 100 | 90 | 36 | 92 | 41 | 95 | 44 | 43 | 25 |

| | | | 48 | 49 | 50 | 51 | 52 | 53 | 54 | 55 | 56 | 57 | 58 | 59 | 60 | 61 | 62 | 63 | 64 |
|---|---|---|---|---|---|---|---|---|---|---|---|---|---|---|---|---|---|---|---|
| Amount of | Compound A | | | | | | | | | | | | | | | | | | |
| Active Ingredients | Compound B | I | | | | | | | | | | | | | | | | | |
| (g/100 kg-dry seed) | | II | 26 | 10 | | | | | | | | | | | | | | | |
| | | III | | | 26 | 10 | | | | | | | | | | | | | |
| | | IV | | | | | 26 | 10 | | | | | | | | | | | |
| | | V | | | | | | | 26 | 10 | | | | | | | | | |
| | | VI | | | | | | | | | 26 | 10 | | | | | | | |
| | | VII | | | | | | | | | | | 26 | 10 | | | | | |
| | Compound C | | | | | | | | | | | | | | 26 | 10 | | | |
| | Compound D | | | | | | | | | | | | | | | | 26 | 5 | |
| | Benlate T ®*¹ | | | | | | | | | | | | | | | | | | 100 |
| (−)-Enantiomer Content in Compound A (% by weight) | | | | | | | | | | | | | | | | | | | |
| Percentage of | a*² | | 92 | 41 | 90 | 40 | 93 | 43 | 94 | 41 | 89 | 38 | 98 | 44 | 0 | 0 | 0 | 0 | 100 |
| Healthy Seedlings | b*³ | | 40 | 21 | 38 | 19 | 40 | 21 | 43 | 23 | 37 | 20 | 65 | 38 | 0 | 0 | 0 | 0 | 70 |

| | | 65 | 0* | 00** |
|---|---|---|---|---|
| Amount of Active Ingredients (g/100 kg-dry seed) | Compound A | | | |
| | Compound B  I | | | |
| | II | | | |
| | III | | | |
| | IV | | | |
| | V | | | |
| | VI | | | |
| | VII | | | |
| | Compound C | | | |
| | Compound D | | | |
| | Benlate T ®*¹ | 50 | | |
| (−)-Enantiomer Content in Compound A (% by weight) | | | | |
| Percentage of | a*² | 93 | 0 | 100 |
| Healthy Seedlings | b*³ | 48 | 0 | 100 |

*Inoculation and no treatment
**No inoculation and no treatment
*¹Commercially available seed disinfectant (a mixture of benomyl and thiram)
*²The case where unhulled rice infected with benomyl-sensitive fungi was used.
*³The case where unhulled rice infected with benomyl-resistant fungi was used.

Test Example 8

Grains of unhulled rice (variety: Nipponbare) infected with *Cochliobolus miyabeanus* were dust-coated with a prescribed amount of each of dusts of the present invention prepared according to Formulation Examples 4 to 6. Thereafter, the unhulled rice was sown in sandy loam in a plastic pot at a rate of 50 grains per pot, covered with soil and cultivated for 21 days in a greenhouse. Then, the symptoms of the disease was examined and the percentage of healthy seedlings was calculated in the same manner as in Test Example 1. The results are shown in Table 8.

TABLE 8

| | | | 1 | 2 | 3 | 4 | 5 | 6 | 7 | 8 | 9 | 10 | 11 | 12 |
|---|---|---|---|---|---|---|---|---|---|---|---|---|---|---|
| Amount of | Compound A | | 1 | 1 | 1 | 1 | 1 | 1 | 1 | 1 | 1 | 1 | 1 | 1 |
| Active Ingredients | Compound B | I | 10 | 10 | 10 | | | | | | | | | |
| (g/100 kg-dry seed) | | II | | | | 10 | 10 | 10 | | | | | | |
| | | III | | | | | | | 10 | 10 | 10 | | | |

TABLE 8-continued

|  |  |  |  |  |  |  |  |  |  |  |  |  |  |
|---|---|---|---|---|---|---|---|---|---|---|---|---|---|
|  |  | IV |  |  |  |  |  |  |  | 10 |  |  |  |
|  |  | V |  |  |  |  |  |  |  |  | 10 |  |  |
|  |  | VI |  |  |  |  |  |  |  |  |  |  | 10 |
|  |  | VII |  |  |  |  |  |  |  |  |  |  |  |
|  | Compound C |  |  |  |  |  |  |  |  |  |  |  |  |
|  | Compound D |  |  |  |  |  |  |  |  |  |  |  |  |
| (−)-Enantiomer Content in Compound A (% by weight) |  |  | 66.5 | 90.2 | 94.7 | 66.5 | 90.2 | 94.7 | 66.5 | 90.2 | 94.7 | 66.5 | 66.5 | 66.5 |
| Percentage of | Found |  | 61 | 68 | 70 | 62 | 67 | 69 | 59 | 68 | 69 | 58 | 59 | 56 |
| Healthy Seedlings | Expected |  | 18 | 20 | 22 | 16 | 18 | 20 | 16 | 18 | 19 | 17 | 16 | 15 |

|  |  |  | 13 | 14 | 15 | 16 | 17 | 18 | 19 | 20 | 21 | 22 | 23 | 24 |
|---|---|---|---|---|---|---|---|---|---|---|---|---|---|---|
| Amount of | Compound A |  | 1 | 1 | 1 | 1 | 1 | 1 | 1 | 1 | 1 | 1 | 1 | 1 |
| Active Ingredients | Compound B | I |  |  |  | 10 |  |  |  |  |  |  |  |  |
| (g/100 kg-dry seed) |  | II |  |  |  |  | 10 | 10 | 10 |  |  |  |  |  |
|  |  | III |  |  |  |  |  |  |  | 10 |  |  |  |  |
|  |  | IV |  |  |  |  |  |  |  |  | 10 |  |  |  |
|  |  | V |  |  |  |  |  |  |  |  |  | 10 |  |  |
|  |  | VI |  |  |  |  |  |  |  |  |  |  | 10 |  |
|  |  | VII | 10 | 10 | 10 |  |  |  |  |  |  |  |  | 10 |
|  | Compound C |  |  |  |  | 5 | 5 | 5 | 5 | 5 | 5 | 5 | 5 | 5 |
|  | Compound D |  |  |  |  |  |  |  |  |  |  |  |  |  |
| (−)-Enantiomer Content in Compound A (% by weight) |  |  | 66.5 | 90.2 | 94.7 | 66.5 | 66.5 | 90.2 | 94.7 | 66.5 | 66.5 | 66.5 | 66.5 | 66.5 |
| Percentage of | Found |  | 62 | 69 | 71 | 85 | 88 | 91 | 93 | 82 | 85 | 84 | 81 | 84 |
| Healthy Seedlings | Expected |  | 17 | 19 | 21 | 33 | 32 | 33 | 35 | 31 | 32 | 31 | 30 | 32 |

|  |  |  | 25 | 26 | 27 | 28 | 29 | 30 | 31 | 32 | 33 | 34 | 35 |
|---|---|---|---|---|---|---|---|---|---|---|---|---|---|
| Amount of | Compound A |  | 1 | 1 | 1 | 1 | 1 | 1 | 1 | 1 | 1 | 1 | 1 |
| Active Ingredients | Compound B | I |  |  |  | 10 |  |  |  |  |  |  |  |
| (g/100 kg-dry seed) |  | II |  |  |  |  | 10 | 10 | 10 |  |  |  |  |
|  |  | III |  |  |  |  |  |  |  | 10 | 10 | 10 |  |
|  |  | IV |  |  |  |  |  |  |  |  |  |  | 10 |
|  |  | V |  |  |  |  |  |  |  |  |  |  |  |
|  |  | VI |  |  |  |  |  |  |  |  |  |  | 10 |
|  |  | VII | 10 | 10 |  |  |  |  |  |  |  |  |  |
|  | Compound C |  | 5 | 5 | 5 | 5 | 5 | 5 | 5 | 5 | 5 | 5 | 5 |
|  | Compound D |  |  |  | 5 | 5 | 5 | 5 | 5 | 5 | 5 | 5 | 5 |
| (−)-Enantiomer Content in Compound A (% by weight) |  |  | 90.2 | 94.7 | 66.5 | 66.5 | 90.2 | 94.7 | 66.5 | 90.2 | 94.7 | 66.5 | 66.5 |
| Percentage of | Found |  | 93 | 95 | 91 | 93 | 98 | 100 | 90 | 97 | 100 | 92 | 91 |
| Healthy Seedlings | Expected |  | 34 | 35 | 33 | 32 | 33 | 35 | 31 | 32 | 34 | 32 | 31 |

|  |  |  | 36 | 37 | 38 | 39 | 40 | 41 | 42 | 43 | 44 | 45 | 46 | 47 |
|---|---|---|---|---|---|---|---|---|---|---|---|---|---|---|
| Amount of | Compound A |  | 1 | 1 | 1 | 1 | 21 | 1 | 21 | 1 | 21 | 1 |  |  |
| Active Ingredients | Compound B | I |  |  |  |  |  |  |  |  |  |  | 21 | 10 |
| (g/100 kg-dry seed) |  | II |  |  |  |  |  |  |  |  |  |  |  |  |
|  |  | III |  |  |  |  |  |  |  |  |  |  |  |  |
|  |  | IV |  |  |  |  |  |  |  |  |  |  |  |  |
|  |  | V |  |  |  |  |  |  |  |  |  |  |  |  |
|  |  | VI | 10 |  |  |  |  |  |  |  |  |  |  |  |
|  |  | VII |  | 10 | 10 | 10 |  |  |  |  |  |  |  |  |
|  | Compound C |  | 5 | 5 | 5 | 5 |  |  |  |  |  |  |  |  |
|  | Compound D |  | 5 | 5 | 5 | 5 |  |  |  |  |  |  |  |  |
| (−)-Enantiomer Content in Compound A (% by weight) |  |  | 66.5 | 66.5 | 90.2 | 94.7 | 66.5 | 66.5 | 90.2 | 90.2 | 94.7 | 94.7 |  |  |
| Percentage of | Found |  | 90 | 92 | 99 | 100 | 20 | 13 | 23 | 15 | 25 | 17 | 15 | 6 |
| Healthy Seedlings | Expected |  | 30 | 32 | 34 | 35 |  |  |  |  |  |  |  |  |

|  |  |  | 48 | 49 | 50 | 51 | 52 | 53 | 54 | 55 | 56 | 57 | 58 | 59 | 60 | 61 | 62 | 63 | 0* |
|---|---|---|---|---|---|---|---|---|---|---|---|---|---|---|---|---|---|---|---|
| Amount of | Compound A |  |  |  |  |  |  |  |  |  |  |  |  |  |  |  |  |  |  |
| Active Ingredients | Compound B | I |  |  |  |  |  |  |  |  |  |  |  |  |  |  |  |  |  |
| (g/100 kg-dry seed) |  | II | 21 | 10 |  |  |  |  |  |  |  |  |  |  |  |  |  |  |  |
|  |  | III |  |  | 21 | 10 |  |  |  |  |  |  |  |  |  |  |  |  |  |
|  |  | IV |  |  |  |  | 21 | 10 |  |  |  |  |  |  |  |  |  |  |  |
|  |  | V |  |  |  |  |  |  | 21 | 10 |  |  |  |  |  |  |  |  |  |
|  |  | VI |  |  |  |  |  |  |  |  | 21 | 10 |  |  |  |  |  |  |  |
|  |  | VII |  |  |  |  |  |  |  |  |  |  | 21 | 10 |  |  |  |  |  |
|  | Compound C |  |  |  |  |  |  |  |  |  |  |  |  |  | 21 | 5 |  |  |  |
|  | Compound D |  |  |  |  |  |  |  |  |  |  |  |  |  |  |  | 21 | 5 |  |
| (−)-Enantiomer Content in Compound A (% by weight) |  |  |  |  |  |  |  |  |  |  |  |  |  |  |  |  |  |  |  |
| Percentage of | Found |  | 13 | 4 | 12 | 3 | 16 | 5 | 14 | 3 | 10 | 2 | 13 | 5 | 30 | 18 | 0 | 0 | 0 |
| Healthy Seedlings | Expected |  |  |  |  |  |  |  |  |  |  |  |  |  |  |  |  |  |  |

00**

|  |  |  |
|---|---|---|
| Amount of | Compound A |  |
| Active Ingredients | Compound B | I |
| (g/100 kg-dry seed) |  | II |
|  |  | III |
|  |  | IV |
|  |  | V |
|  |  | VI |
|  |  | VII |
|  | Compound C |  |
|  | Compound D |  |
| (−)-Enantiomer Content in Compound A (% by weight) |  |  |

TABLE 8-continued

| | Percentage of Healthy Seedlings | Found Expected | 100 |
|---|---|---|---|

*Inoculation and no treatment
**No inoculation and no treatment

Test Example 9

Grains of unhulled rice (variety: Nipponbare) infected with *Pseudomonas glumae* were dust-coated with a prescribed amount of each of dusts of the present invention prepared according to Formulation Examples 1 to 3. Thereafter, the unhulled rice was sown in sandy loam in a plastic pot at a rate of 50 grains per pot, covered with soil and cultivated for 21 days in a greenhouse. Then, the symptoms of the disease was examined and the percentage of healthy seedlings was calculated in the same manner as in Test Example 1. The results are shown in Table 9.

TABLE 2

| | | | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|
| Amount of Active Ingredients (g/100 kg-dry seed) | Compound A | | 1 | 1 | 1 | 1 | 1 | 1 | 1 | 1 | 1 | 1 | 1 | 1 | 1 | 1 |
| | Compound B | I | 5 | 5 | 5 | | | | | | | | | | | |
| | | II | | | | 5 | 5 | 5 | | | | | | | | |
| | | III | | | | | | | 5 | 5 | 5 | | | | | |
| | | IV | | | | | | | | | | 5 | | | | |
| | | V | | | | | | | | | | | 5 | | | |
| | | VI | | | | | | | | | | | | 5 | | |
| | | VII | | | | | | | | | | | | | 5 | 5 |
| | Compound C | | | | | | | | | | | | | | | |
| | Compound D | | | | | | | | | | | | | | | |
| (−)-Enantiomer Content in Compound A (% by weight) | | | 66.5 | 90.2 | 94.7 | 66.5 | 90.2 | 94.7 | 66.5 | 90.2 | 94.7 | 66.5 | 66.5 | 66.5 | 66.5 | 90.2 |
| Percentage of Healthy Seedlings | Found | | 25 | 28 | 30 | 23 | 27 | 32 | 20 | 24 | 29 | 21 | 23 | 19 | 26 | 29 |
| | Expected | | 0 | 0 | 0 | 0 | 0 | 0 | 0 | 0 | 0 | 0 | 0 | 0 | 0 | 0 |

| | | | 15 | 16 | 17 | 18 | 19 | 20 | 21 | 22 | 23 | 24 | 25 | 26 | 27 | 28 |
|---|---|---|---|---|---|---|---|---|---|---|---|---|---|---|---|---|
| Amount of Active Ingredients (g/100 kg-dry seed) | Compound A | | 1 | 1 | 1 | 1 | 1 | 1 | 1 | 1 | 1 | 1 | 1 | 1 | 1 | 1 |
| | Compound B | I | | 5 | | | | | | | | | | | 5 | |
| | | II | | | 5 | 5 | 5 | | | | | | | | | 5 |
| | | III | | | | | | 5 | | | | | | | | |
| | | IV | | | | | | | 5 | | | | | | | |
| | | V | | | | | | | | 5 | | | | | | |
| | | VI | | | | | | | | | 5 | | | | | |
| | | VII | 5 | | | | | | | | | 5 | 5 | 5 | | |
| | Compound C | | | 5 | 5 | 5 | 5 | 5 | 5 | 5 | 5 | 5 | 5 | 5 | 5 | 5 |
| | Compound D | | | | | | | | | | | | | | 10 | 10 |
| (−)-Enantiomer Content in Compound A (% by weight) | | | 94.7 | 66.5 | 66.5 | 90.2 | 94.7 | 66.5 | 66.5 | 66.5 | 66.5 | 66.5 | 90.2 | 94.7 | 66.5 | 66.5 |
| Percentage of Healthy Seedlings | Found | | 33 | 29 | 31 | 33 | 34 | 25 | 23 | 26 | 22 | 29 | 32 | 33 | 95 | 94 |
| | Expected | | 0 | 0 | 0 | 0 | 0 | 0 | 0 | 0 | 0 | 0 | 0 | 0 | 43 | 43 |

| | | | 29 | 30 | 31 | 32 | 33 | 34 | 35 | 36 | 37 | 38 | 39 | 40 | 41 | 42 |
|---|---|---|---|---|---|---|---|---|---|---|---|---|---|---|---|---|
| Amount of Active Ingredients (g/100 kg-dry seed) | Compound A | | 1 | 1 | 1 | 1 | 1 | 1 | 1 | 1 | 1 | 1 | 1 | 21 | 1 | 21 |
| | Compound B | I | | | | | | | | | | | | | | |
| | | II | 5 | 5 | | | | | | | | | | | | |
| | | III | | | 5 | 5 | 5 | | | | | | | | | |
| | | IV | | | | | | 5 | | | | | | | | |
| | | V | | | | | | | 5 | | | | | | | |
| | | VI | | | | | | | | 5 | | | | | | |
| | | VII | | | | | | | | | 5 | 5 | 5 | | | |
| | Compound C | | 5 | 5 | 5 | 5 | 5 | 5 | 5 | 5 | 5 | 5 | 5 | | | |
| | Compound D | | 10 | 10 | 10 | 10 | 10 | 10 | 10 | 10 | 10 | 10 | 10 | | | |
| (−)-Enantiomer Content in Compound A (% by weight) | | | 90.2 | 94.7 | 66.5 | 90.2 | 94.7 | 66.5 | 66.5 | 66.5 | 66.5 | 90.2 | 94.7 | 66.5 | 66.5 | 90.2 |
| Percentage of Healthy Seedlings | Found | | 98 | 100 | 95 | 99 | 100 | 97 | 93 | 91 | 98 | 100 | 100 | 3 | 0 | 6 |
| | Expected | | 43 | 43 | 43 | 43 | 43 | 43 | 43 | 43 | 43 | 43 | 43 | | | |

| | | | 43 | 44 | 45 | 46 | 47 | 48 | 49 | 50 | 51 | 52 | 53 | 54 | 55 | 56 | 57 | 58 | 59 | 60 | 61 | 62 |
|---|---|---|---|---|---|---|---|---|---|---|---|---|---|---|---|---|---|---|---|---|---|---|
| Amount of Active Ingredients (g/100 kg-dry seed) | Compound A | | 1 | 21 | 1 | | | | | | | | | | | | | | | | | |
| | Compound B | I | | | | 21 | 5 | | | | | | | | | | | | | | | |
| | | II | | | | | | 21 | 5 | | | | | | | | | | | | | |
| | | III | | | | | | | | 21 | 5 | | | | | | | | | | | |
| | | IV | | | | | | | | | | 21 | 5 | | | | | | | | | |
| | | V | | | | | | | | | | | | 21 | 5 | | | | | | | |
| | | VI | | | | | | | | | | | | | | 21 | 5 | | | | | |
| | | VII | | | | | | | | | | | | | | | | 21 | 5 | | | |
| | Compound C | | | | | | | | | | | | | | | | | | | 21 | 5 | |
| | Compound D | | | | | | | | | | | | | | | | | | | | | 21 |
| (−)-Enantiomer Content in Compound A (% by weight) | | | 90.2 | 94.7 | 94.7 | | | | | | | | | | | | | | | | | |
| Percentage of Healthy Seedlings | Found | | 0 | 7 | 0 | 5 | 0 | 4 | 0 | 2 | 0 | 3 | 0 | 3 | 0 | 0 | 0 | 8 | 0 | 10 | 0 | 58 |
| | Expected | | | | | | | | | | | | | | | | | | | | | |

| | | 63 | 0* | 00** |
|---|---|---|---|---|
| | Amount of | | | |
| | Compound A | | | |

TABLE 2-continued

| | | | | |
|---|---|---|---|---|
| Active Ingredients (g/100 kg-dry seed) | Compound B | I | | |
| | | II | | |
| | | III | | |
| | | IV | | |
| | | V | | |
| | | VI | | |
| | | VII | | |
| | Compound C | | | |
| | Compound D | 10 | | |
| (−)-Enantiomer Content in Compound A (% by weight) | | | | |
| Percentage of Healthy Seedlings | Found | 43 | 0 | 100 |
| | Expected | | | |

*Inoculation and no treatment
**No inoculation and no treatment

What is claimed is:

1. A seed disinfectant composition comprising fungicidally effective amounts of
   (A) (E)-1-(2,4-dichlorophenyl)-4,4-dimethyl-2-(1,2,4-triazol-1-yl)-1-penten-3-ol containing not less than 66.5% by weight of (−)-(E)-1-(2,4-dichlorophenyl)-4,4-dimethyl-2-(1,2,4-triazol-1-yl)-1-penten-3-ol and
   (B) at least one benzimidazole thiophanate fungicide, wherein the weight ratio of (A):(B) is 1–50:1–50.

2. A seed disinfectant composition according to claim 1, wherein the content of (−)-(E)-1-(2,4-dichlorophenyl)-4,4-dimethyl-2-(1,2,4-triazol-1-yl)-1-penten-3-ol in (A) is not less than 80% by weight.

3. A seed disinfectant composition according to claim 1, wherein (A) is substantially pure (−)-(E)-1-(2,4-dichlorophenyl)-4,4-dimethyl-2-(1,2,4-triazol-1-yl)-1-penten-3-ol.

4. A seed disinfectant composition according to claim 1, wherein Compound B is at least one member selected from the group consisting of methyl 1-(butylcarbamoyl)benzimidazol-2-ylcarbamate, 2-(4-thiazolyl)-benzimidazole, methyl benzimidazol-2-ylcarbamate, 2-(2-furyl)benzimidazole, 1,2-bis(3-methoxycarbonyl-2-thioureido)benzene, 1,2-bis(3-ethoxycarbonyl-2-thioureido)benzene and methyl 1-(2-cyclohexenylcarbamoyl)-2-benzimidazolecarbamate.

5. A seed disinfectant composition according to claim 1, wherein the weight ratio of (A):(B) is 1–20:1–20.

6. A seed disinfectant composition according to claim 1, which further comprises
   (C) O,O-dimethyl-O-(2,6-dichloro-4-methylphenyl)-phosphorothioate.

7. A seed disinfectant composition according to claim 1, which further comprises
   (C) O,O-dimethyl-O-(2,6-dichloro-4-methylphenyl)-phosphorothioate and
   (D) 1-Ethyl-1,4-dihydro-6,7-methylenedioxy-4-oxo-3-quinoline carboxylic acid or a salt thereof.

8. A seed disinfectant composition according to claim 6, wherein the weight ratio of (A):(B):(C) is 1–50:1–50:>0–50.

9. A seed disinfectant composition according to claim 7, wherein the weight ratio of (A):(B):(C):(D) is 1–50:1–50:>0–50:>0–50.

10. A seed disinfectant composition according to claim 7, wherein the weight ratio of (A):(B):(C):(D) is 1–20:1–20:1–20:1–20.

11. A seed disinfectant composition according to claim 1, 6 or 7, which further comprises at least one inert carrier.

12. A seed disinfectant dust comprising active ingredients according to claim 1, 6 or 7, at least one solid inert carrier and optionally hydroxyisoxazole or imazalil.

13. A seed disinfectant wettable powder comprising active ingredients according to claim 1, 6 or 7, a wetting agent, a dispersant, at least one solid carrier and optionally hydroxyisoxazole or imazalil.

14. A seed disinfectant flowable concentrate comprising active ingredients according to claim 1, 6 or 7, surface active agents, at least one liquid carrier and optionally hydroxyisoxazole or imazalil.

15. A seed disinfectant emulsifiable concentrate comprising active ingredients according to claim 1 or 6, at least one surface active agent, at least one liquid carrier and optionally hydroxyisoxazole or imazalil.

16. A seed disinfectant composition according to claim 10, wherein the active ingredient concentration is 0.1–99.9% by weight based on the total weight of the composition.

17. A seed disinfectant composition according to claim 10, wherein the active ingredient concentration is 0.1–80% by weight based on the total weight of the composition.

18. A method for treating or preventing fungal infection of seeds which comprises applying a fungicidally effective amount of the seed disinfectant composition according to claim 1, 6 or 7 to the seeds.

19. A method according to claim 18, wherein the seed disinfectant composition is applied to the seeds at an active ingredient application rate of 0.00005–1% based on the dry weight of seeds.

* * * * *